United States Patent
Choi et al.

(10) Patent No.: US 9,649,173 B2
(45) Date of Patent: May 16, 2017

(54) SURGICAL DEVICE

(75) Inventors: Hyun-do Choi, Yongin-si (KR); Yeon-ho Kim, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 893 days.

(21) Appl. No.: 13/404,920

(22) Filed: Feb. 24, 2012

(65) Prior Publication Data

US 2012/0310252 A1 Dec. 6, 2012

(30) Foreign Application Priority Data

Jun. 3, 2011 (KR) .................. 10-2011-0054147

(51) Int. Cl.
A61B 34/30 (2016.01)
(52) U.S. Cl.
CPC ........ *A61B 34/30* (2016.02); *A61B 2034/302* (2016.02); *A61B 2034/305* (2016.02)
(58) Field of Classification Search
CPC ............ A61B 19/2023; A61B 19/2234; A61B 19/2203; A61B 19/2238; A61B 19/201; A61B 2017/00398; A61B 2017/2927; A61B 2019/2207; A61B 2019/2211; A61B 2019/2215; A61B 2019/2219; A61B 2019/2223; A61B 2019/2234; A61B 2019/2238; A61B 2019/2242; A61B 2019/2249; A61B 2017/2902; A61B 2017/2912; A61B 2017/2929; A61B 2017/293; A61B 2034/301; A61B 2034/305; A61B 2034/302; A61B 34/30; B25J 18/007; B25J 15/022; B25J 7/00; B25J 9/06

USPC ...... 606/130, 169, 170, 207; 901/23, 28, 30, 901/31, 29, 16; 318/568.11, 568.12; 600/429, 417

See application file for complete search history.

(56) References Cited

U.S. PATENT DOCUMENTS

| 4,870,306 | A | * | 9/1989 | Petersen ................... 310/12.31 |
| 5,841,950 | A | * | 11/1998 | Wang et al. .................. 700/264 |
| 6,325,808 | B1 | * | 12/2001 | Bernard ............. A61B 17/0469 |
| | | | | 318/568.11 |
| 6,394,998 | B1 | | 5/2002 | Wallace et al. |
| 2002/0133174 | A1 | * | 9/2002 | Charles .................. A61B 34/30 |
| | | | | 606/130 |

(Continued)

FOREIGN PATENT DOCUMENTS

| JP | 2002-166385 | 6/2002 |
| JP | 2005-169602 | 6/2005 |

(Continued)

*Primary Examiner* — Jocelin Tanner
(74) *Attorney, Agent, or Firm* — Harness, Dickey & Pierce, P.L.C.

(57) ABSTRACT

A surgical device, the surgical device including a mounting part mounted on a robot arm of a surgical robot; an extension part extending from the mounting part; a joint driving part that comprises a driving motor having a driving axis, that comprises a driving rod connected to the driving axis and reciprocating, and that is connected to an end of the extension part; and a joint part that is connected to the joint driving part, that is driven at one or more degrees of freedom by the driving rod, wherein the driving motor is connected to the driving axis with an elastic connection member.

16 Claims, 7 Drawing Sheets

(56) References Cited

U.S. PATENT DOCUMENTS

2006/0020279 A1* 1/2006 Chauhan et al. ............. 606/167
2009/0216248 A1* 8/2009 Uenohara .............. A61B 17/29
   606/130

FOREIGN PATENT DOCUMENTS

KR  10-2010-0045556   5/2010
KR  10-2010-0110134   10/2010

* cited by examiner

FIG. 13

SURGICAL DEVICE

CROSS-REFERENCE TO RELATED APPLICATIONS

This application claims the priority benefit of Korean Patent Application No. 10-2011-0054147, filed on Jun. 3, 2011, in the Korean Intellectual Property Office, the disclosure of which is incorporated herein in its entirety by reference.

BACKGROUND

1. Field

The present disclosure relates to a surgical device that is mounted on a robot arm of a surgical robot, that is inserted into a human body, and that has at least one joint part.

2. Description of the Related Art

A surgical robot is a robot that performs a minimally invasive surgery by using a small surgical tool to insert into a human body. The surgical robot has a plurality of robot arms. A robot arm may include a passive arm that is manually operated during preparation before a surgical operation, and an active arm that is operated according to the motion of an operator during a surgical operation. A surgical device is mounted to the active arm so as to be inserted into an abdominal cavity, a joint, or the like, and then to perform a surgical operation including internal photographing, excision, etc. The surgical device may have at least one joint part so as to effectively access an affected part. The joint part is operated by a cable extending to the active arm, and the active arm includes a driver so as to drive the cable.

SUMMARY

When a joint part of a surgical device is driven by using a cable, if the number of joint parts is increased, the number of cables is increased proportionally, so that a mechanical structure of the surgical device in which drivers are mounted to drive the cables may be complicated. In the surgical device formed of a plurality of joints, movement of a cable to drive a last joint may affect movement of other joints. This problem increases as the number of joints is increased. As a distance between the surgical device and a driver arranged in an active arm increases, backlash may increase. In order to decrease the backlash, large tension is applied to a cable, and in this regard, if the cable is permanently deformed due to use for a long time, driving accuracy of the joint parts may deteriorate.

Additional aspects will be set forth in part in the description which follows and, in part, will be apparent from the description, or may be learned by practice of the presented embodiments.

According to an aspect of the present disclosure, a surgical device includes a mounting part mounted on a robot arm of a surgical robot; an extension part shape extending from the mounting part; a joint driving part that comprises a driving motor having a driving axis that comprises a driving rod connected to the driving axis and reciprocating, and that is connected to an end of the extension part; and a joint part that is connected to the joint driving part, that is driven at one or more degrees of freedom by the driving rod, wherein the driving motor is connected to the driving axis with an elastic connection member.

The elastic connection member may contact an end of the driving axis while the elastic connection member applies a pre-load to the end of the driving axis.

The driving motor may include a linear motor that linearly reciprocates the driving axis, and the elastic connection member may include first and second connecting members of which ends are connected to the driving rod and of which the other ends elastically contact ends of the driving axis in an axial direction of the driving axis.

The linear motor may include an ultrasonic motor.

The driving motor may include a plurality of the linear motors that linearly reciprocate the driving axis, and the elastic connection member may include a plurality of first and second connecting members of which ends are connected to the driving rod and of which the other ends elastically contact ends of the driving axis in an axial direction of the driving axis.

The joint driving part may include a plurality of the driving rods which correspond to the number of the one or more degrees of freedom of the joint part, and comprises a plurality of the driving motors for driving the plurality of the driving rods.

According to another aspect of the present disclosure, a surgical device includes a mounting part mounted on a robot arm of a surgical robot; an extension part extending from the mounting part; and a joint assembly that has a bar shape, that comprises a joint part having one or more degrees of freedom, and that comprises a joint driving part having a driving motor so as to drive the joint part.

The joint driving part may include a housing having a bar shape; and a driving rod that is mounted in the housing so as to reciprocate in a longitudinal direction of the housing by the driving motor, and that is a rigid body connected to the joint part with one or more link arms.

The driving motor may include a linear motor that has a driving axis reciprocating in the longitudinal direction of the housing and that is fixed in the housing, and the joint driving part may include a connecting member that connects the driving axis and the driving rod.

The connection member may include first and second connecting members of which ends are connected to the driving rod and of which the other ends elastically contact ends of the driving axis while the other ends apply a pre-load to the ends of the driving axis.

The driving motor may include a plurality of the linear motors that are connected to the driving rod by using a plurality of first and second connecting members of which ends are connected to the driving rod and of which the other ends elastically contact ends of the driving axis while the other ends apply a pre-load to the ends of the driving axis.

The driving axes of the plurality of the linear motors may be in parallel with a plurality of the driving rods.

The joint driving part may include a plurality of the driving rods which correspond to the number of the one or more degrees of freedom of the joint part, and may include a plurality of the driving motors for driving the plurality of the driving rods.

The driving motor may include an ultrasonic motor.

The surgical device may further include a plurality of the joint assemblies, the plurality of the joint assemblies may be sequentially connected from the extension part, and a surgical tool may be mounted on the joint assembly that is the outermost from among the plurality of the joint assemblies.

According to another aspect of the present disclosure, a system is provided, including a surgical robot including at least one robot arm; and a surgical device mounted on the at least one robot arm, wherein the surgical device includes a mounting part to mount on the at least one robot arm; an extension part to extend from the mounting part; and a joint assembly that has a bar shape, comprising a joint part having one or more degrees of freedom, and a joint driving part having a driving motor so as to drive the joint part.

The joint driving part may include a housing having a bar shape; and a driving rod that is mounted in the housing so as to reciprocate in a longitudinal direction of the housing by the driving motor, and that is a rigid body connected to the joint part with one or more link arms.

The driving motor may include a linear motor that has a driving axis reciprocating in the longitudinal direction of the housing and that is fixed in the housing, and wherein the joint driving part comprises a connecting member that connects the driving axis and the driving rod.

Further, a crosstalk between plural joint parts may be removed by matching a rotation axis of at least one of the one or more link arms with a rotation axis of a respective joint part.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In the drawings, like reference numerals in the drawings denote like elements, and the size of each component may be exaggerated for clarity. As used herein, the term "and/or" includes any and all combinations of one or more of the associated listed items.

Figure 1:
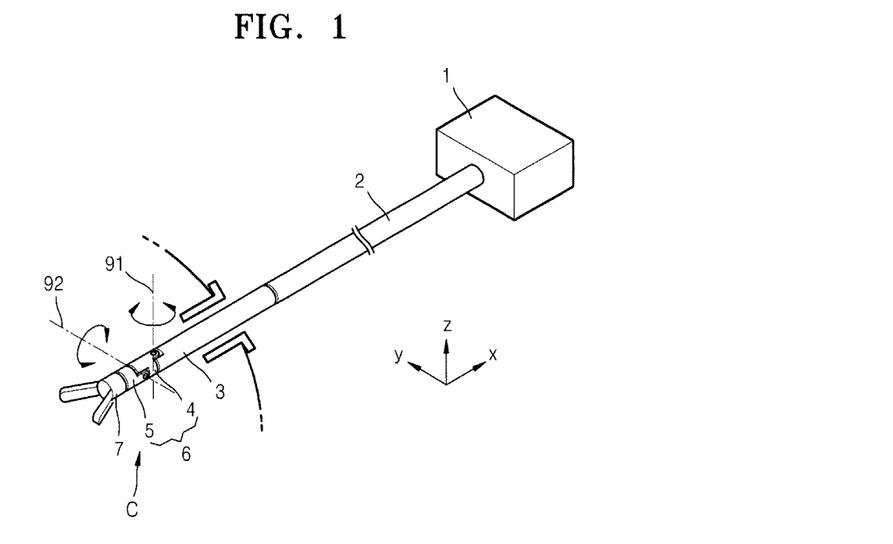
FIG. 1 is a perspective view of a surgical device including a joint part, according to an example embodiment.

FIG. 1 is a perspective view of a surgical device according to an example embodiment of the present disclosure. Referring to FIG. 1, the surgical device includes a mounting part 1 to be mounted on a robot arm of a surgical robot (not shown), and an extension part 2 extending from the mounting part 1. The extension part 2 may have a thin and long bar shaped so as to be inserted into a human body, e.g., an abdominal cavity, a joint, or the like, in order to access an affected part. A joint driving part 3 and a joint part 6 are sequentially connected to an end of the extension part 2. The joint driving part 3 and the joint part 6 may have a thin and long bar shape so as to be easily inserted into the human body, e.g. the abdominal cavity, the joint, or the like, in order to access the affected part. A surgical tool 7 is mounted at an end of the joint part 6 so as to perform a particular surgical operation including excision, suture, or the like by manipulation of an operator. The surgical tool 7 may include a surgical knife, surgical forceps, surgical scissors, a cauter (an instrument that burns or cuts an affected part by using an electric energy or a thermal energy), an endoscope camera, or the like. FIG. 1 illustrates a surgical forceps as a non-limiting example of the surgical tool 7.

The joint part 6 enables the surgical tool 7 to easily access the affected part, and may have at least one degree of freedom. In the present embodiment, the joint part 6 has two degrees of freedom. For example, the joint part 6 has a first joint part 4 rotating around a rotation axis 91 in a Z-direction, and a second joint part 5 rotating around a rotation axis 92 in a Y-direction.

Figure 2:
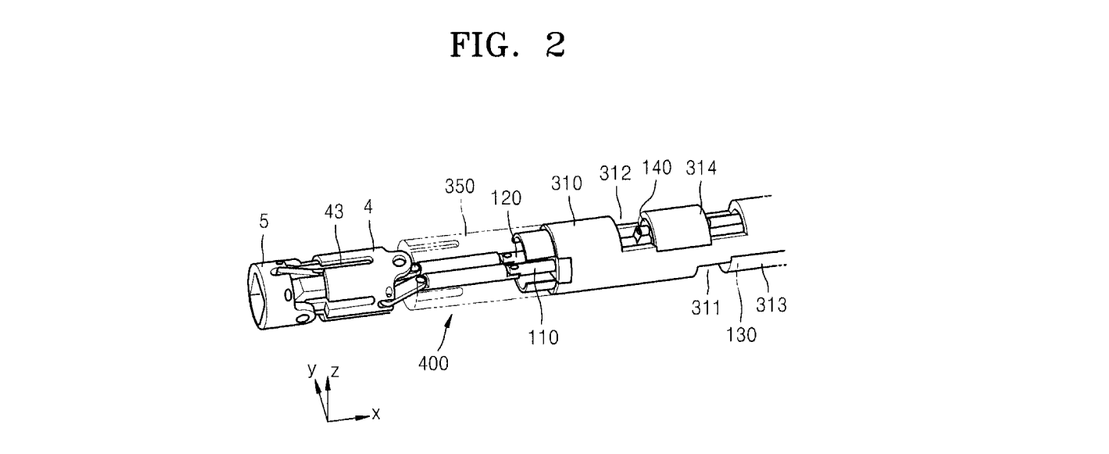
FIG. 2 is a diagram illustrating a "C" portion of FIG. 1 in detail.

FIG. 2 is a diagram illustrating a "C" portion of FIG. 1 in detail. In FIG. 2, the surgical tool 7 is omitted. Referring to FIG. 2, the joint driving part 3 may include first and second driving rods 110 and 120 to drive the first and second joint parts 4 and 5, respectively; first and second linear motors 130 and 140 that are driving motors providing a driving power to reciprocate each of the first and second driving rods 110 and 120; and a link unit 400 that is connected to the first and second driving rods 110 and 120 so as to operate the first and second joint parts 4 and 5.

The first and second driving rods 110 and 120 replace a conventional cable, and are significantly less flexible than the cable. That is, compared to the cable, the first and second driving rods 110 and 120 are relatively rigid bodies. For example, the first and second driving rods 110 and 120 may have a bar shape formed of a material including metal, ceramic, plastic, and the like.

The joint driving part 3 has a housing 310. The housing 310 functions as a frame for combining configuring elements of the joint driving part 3, and may have a long and hollow bar shape in which the configuring elements may be installed. A cross-sectional area shape of the housing 310 may be circular, polygonal, or the like. The housing 310 may form an outer form of the joint driving part 3. The first and second driving rods 110 and 120 are disposed in the housing 310 so as to reciprocate in a longitudinal direction of the housing 310, that is, an X-direction of FIG. 2. For example, referring to FIG. 3, the first and second driving rods 110 and 120 may be supported by a pair of supporting members 320 and 330 disposed at both ends of the housing 310.

Figure 3:
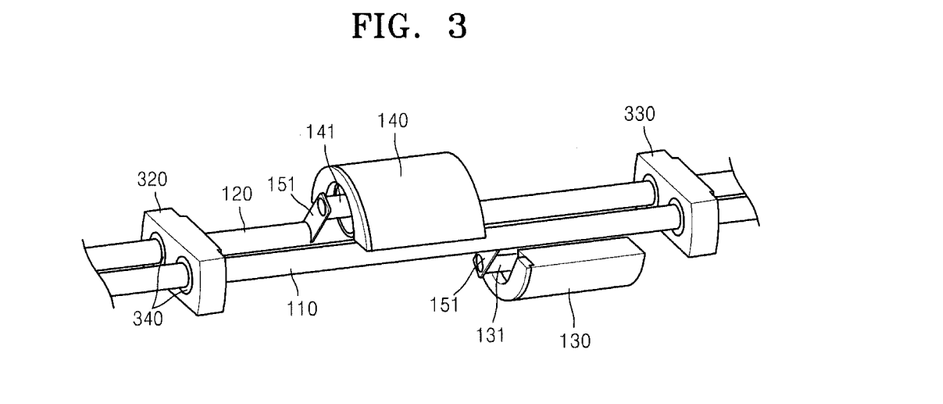
FIG. 3 is a perspective view illustrating arrangement of first and second driving rods, and first and second linear motors, according to another example embodiment.

The supporting members 320 and 330 may have through-holes via which the first and second driving rods 110 and 120 pass, respectively. A plurality of bearing members 340 may be interposed between the through-holes and the first and second driving rods 110 and 120 so as to allow the first and second driving rods 110 and 120 to smoothly reciprocate.

The bearing members 340 may be sintered bearings that have hollow portions for allowing passage of the first and second driving rods 110 and 120 and that include lubricating oil. In addition, the bearing members 340 may be plastic bearings having an excellent sliding characteristic. Although the present embodiment has a structure in which the first and second driving rods 110 and 120 are supported by the supporting members 320 and 330 for reciprocating movement of the first and second driving rods 110 and 120, one or more embodiments are not limited to the structure. If desired, an additional supporting member (not shown) may be disposed between the supporting members 320 and 330.

The first and second linear motors 130 and 140 have driving axes 131 and 141 that linearly reciprocate. One of various types of motors including a linear reciprocation driving axis may be used as the first and second linear motors 130 and 140. For example, the first and second linear motors 130 and 140 may be ultrasonic motors. An ultrasonic motor uses an elastic vibration of a piezoelectric device in an ultrasonic band, and compared to an electromagnetic motor, the ultrasonic motor has a simple structure, so that the ultrasonic motor may be small and light in weight. Also, the ultrasonic motor generates very low noise and is not affected by electromagnetic noise, so that the ultrasonic motor may be useful as a linear motor in a small space that is easily affected by electromagnetic waves.

The first and second linear motors 130 and 140 are fixed in the housing 310. For example, referring to FIG. 2, first and second openings 311 and 312 may be formed in the housing 310, and first and second brackets 313 and 314 having the first and second linear motors 130 and 140 mounted thereto may be combined to the housing 310. Since connection structures between respective first and second driving rods 110 and 120 and respective first and second linear motors 130 and 140 are the same, hereinafter, the connection structure between the first driving rod 110 and the first linear motor 130 is described in detail.

The first driving rod 110 is connected to the driving axis 131 of the first linear motor 130 with an elastic connection member. For example, referring to FIGS. 3 and 4, the elastic connection member may include first and second connecting members 151 and 152. One end 153 of each of the first and second connecting members 151 and 152 is combined to the first driving rod 110. The other ends 154 of the first and second connecting members 151 and 152 are respectively connected to both ends 132 and 133 of the driving axis 131 in an axial direction. In the present embodiment, the other ends 154 of the first and second connecting members 151 and 152 respectively contact the ends 132 and 133 of the driving axis 131. In order to make the driving axis 131 and the first driving rod 110 connect without backlash, that is, in order to allow a reciprocating driving power of the driving axis 131 to be effectively delivered to the first driving rod 110 without delay or loss, it is necessary for the other ends 154 of the first and second connecting members 151 and 152 to maintain contact with the ends 132 and 133 of the driving axis 131. For this, the other ends 154 of the first and second connecting members 151 and 152 may contact the ends 132 and 133 of the driving axis 131 while applying a pre-load to the ends 132 and 133 of the driving axis 131.

Figure 4:
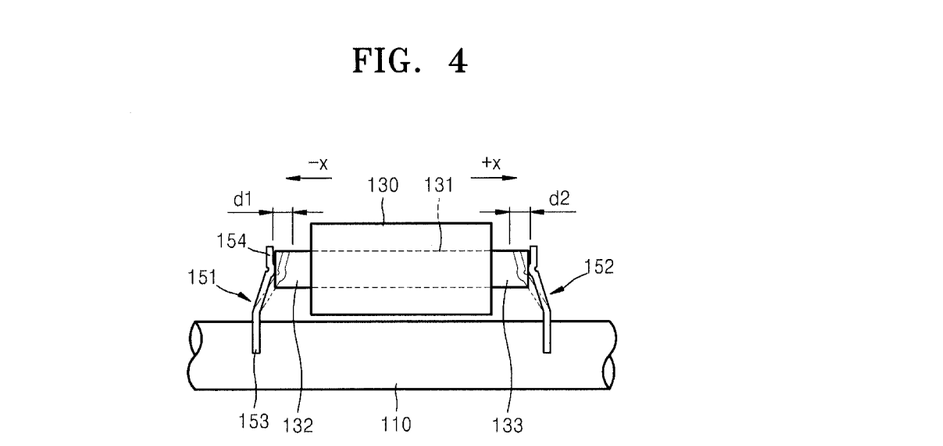
FIG. 4 is side view of a structure for connecting a driving rod and a linear motor, according to another example embodiment.

In order to apply a pre-load, the first and second connecting members 151 and 152 may be formed of a material having elasticity. For example, the first and second connecting members 151 and 152 may be metal thin springs. The ends 153 of the first and second connecting members 151 and 152 may be combined to the first driving rod 110 by using one of a pressing method, a welding method, an adhering method, a coupling method using a fixing member, and the like. Referring to FIG. 4, the first and second connecting members 151 and 152 extend from the ends 153 that are combined to the first driving rod 110. When the first bracket 313 having the first linear motor 130 mounted thereto is combined to the housing 310, the first and second connecting members 151 and 152 elastically contact the ends 132 and 133 of the driving axis 131, respectively, while the first and second connecting members 151 and 152 bend from an initial status of a dashed line in FIG. 4 to a contact status of a solid line in FIG. 4. Thus, the pre-load that is proportional to bend distances d1 and d2 of the first and second connecting members 151 and 152 may be applied to the ends 132 and 133 of the driving axis 131. In the present embodiment, a metal thin spring is used as the first and second connecting members 151 and 152. However, the first and second connecting members 151 and 152 are not limited thereto. Thus, if the pre-load is applied to the ends 132 and 133 of the driving axis 131 as described above, the first and second connecting members 151 and 152 may be formed of another elastic material, e.g., plastic. Additionally, a shape of the first and second connecting members 151 and 152 is not limited to a shape as shown in FIGS. 3 and 4.

When the driving axis 131 reciprocates in −X and +X directions by driving the first linear motor 130, a reciprocating driving power thereof may be delivered to the first driving rod 110 via the first and second connecting members 151 and 152 so as to reciprocate the first driving rod 110 in the −X and +X directions. Since the first and second connecting members 151 and 152 contact the ends 132 and 133 of the driving axis 131 while applying a pre-load to the ends 132 and 133 of the driving axis 131, the reciprocating driving power of the driving axis 131 may be delivered to the first driving rod 110 without delay or loss.

The second linear motor 140 and the second driving rod 120 are connected to each other according to the same connection structure as that of the first linear motor 130 and the first driving rod 110 described above. When the driving axis 141 reciprocates in the −X and +X directions by driving the second linear motor 140, the second driving rod 120 may reciprocate in the −X and +X directions.

Although not illustrated, a control line to control the first and second linear motors 130 and 140 is connected to the surgical robot via the joint driving part 3, the extension part 2, and the mounting part 1.

According to a driving method using the conventional cable, a driver to drive the cable is installed in a robot arm, and a complicated mechanical structure to connect the driver and the cable has to be installed in the robot arm and the mounting part 1. However, according to the surgical device of the present embodiment, the first and second linear motors 130 and 140, which are driving motors that provide the driving power for driving the joint part 6, are directly mounted to the surgical tool 7, so that mechanical connection elements for connection between the surgical device and the robot arm of the surgical robot driving the joint part 6, may be omitted, and thus, structures of the robot arm and the mounting part 1 may be simplified.

In addition, the first and second driving rods 110 and 120 that are driven by the first and second linear motors 130 and 140 are relatively rigid bodies, compared to the conventional cable. Thus, there is a small risk the first and second driving rods 110 and 120 are permanently deformed due to use for a long time. Further, unlike the conventional cable, it is not necessary to apply tension to the first and second driving rods 110 and 120 so that backlash due to damage caused by tension or tension deterioration, which may occur in the conventional cable, does not occur. Thus, compared to the conventional cable, it is possible to stably drive the joint part 6.

The present embodiment corresponds to a case in which one first linear motor 130 is used but one or more embodiments are not limited thereto. For example, when a surgical operation is performed, the surgical tool 7 and the joint part 6 may be inserted into a human body, and even the joint driving part 3 and the extension part 2 may be inserted into the human body. Thus, in order to minimize a size of an incised portion of the human body, a size of a part inserted into the human body, that is, a size of a diameter of the part, may be limited. Therefore, a size of a motor may be limited.

Figure 5:
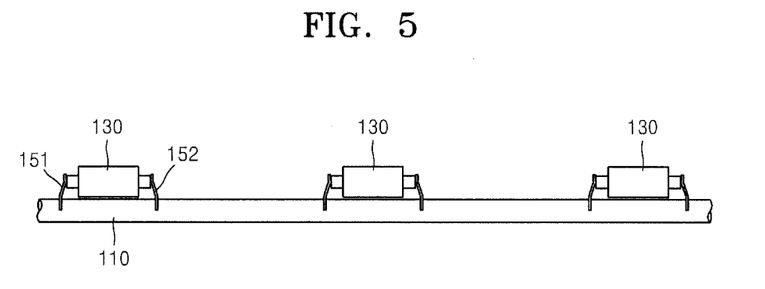
FIG. 5 illustrates a structure for using a plurality of linear motors so as to reciprocate a driving rod, according to another example embodiment.

In order to obtain a desired large driving power in a limited installation space, a plurality of motors may be used. For example, as illustrated in FIG. 5, in order to drive the first driving rod 110, a plurality of the first linear motors 130 that are respectively connected to the first driving rod 110 with their respective first and second connecting members 151 and 152 may be used. In this case, a connection structure in which a pre-load is applied to the driving axis 131 by using the first and second connecting members 151 and 152 allows a driving load for driving the first driving rod 110 to be equally applied to the plurality of the first linear motors 130. In a case where the plurality of the first linear motors 130 are connected to the first driving rod 110 by using a rigid body combination method, due to an error in a manufacturing process and an effort in an assembling process, a connection status between each of the first linear motors 130 and the first driving rod 110 may differ. Thus, a load of the first driving rod 110 may not be delivered or may be partially delivered to a first linear motor 130 that is loosely connected, and the load may be excessively delivered to only a first linear motor 130 that is well connected. Then, a driving power to drive the joint part 6 is insufficient, such that it is difficult to accurately drive the joint part 6. Further, since some first linear motors 130 are excessively used, they may be damaged. However, according to the connection status in the present embodiment, the plurality of the first linear motors 130 are pre-loaded by the first and second connecting members 151 and 152 and then are connected to the first driving rod 110. By doing so, the connection status between each of the plurality of the first linear motors 130 and the first driving rod 110 is uniform, so that a stable driving power may be delivered to the first driving rod 110, and a highly reliable driving function may be maintained during a lifetime of the plurality of the first linear motors 130.

The plurality of the first linear motors 130 are connected in parallel with respect to the first driving rod 110. The parallel connection structure is simpler than a serial connection structure. For a serial connection, it is necessary to segment the first driving rod 110 into a plurality of parts, to dispose the plurality of the first linear motors 130 between each of the segmented parts, and then to connect the segmented parts in series. However, the serial connection causes difficulty in manufacturing and assembling processes. Moreover, the serial connection makes a structure in which the entire first driving rod 110 cannot be driven when one motor is damaged. Compared to the serial connection, when the plurality of the first linear motors 130 are connected in parallel with respect to the first driving rod 110, the first driving rod 110 functions as one part, so that the number of parts may be decreased.

The second driving rod 120 may be connected to a plurality of the second linear motors 140 in the same structure as shown in FIG. 5 and then may be driven.

Next, a structure for driving the first and second joint parts 4 and 5 by using the reciprocating movement of the first and second driving rods 110 and 120 will now be described. The first and second joint parts 4 and 5 may be hollow members.

Figure 6:
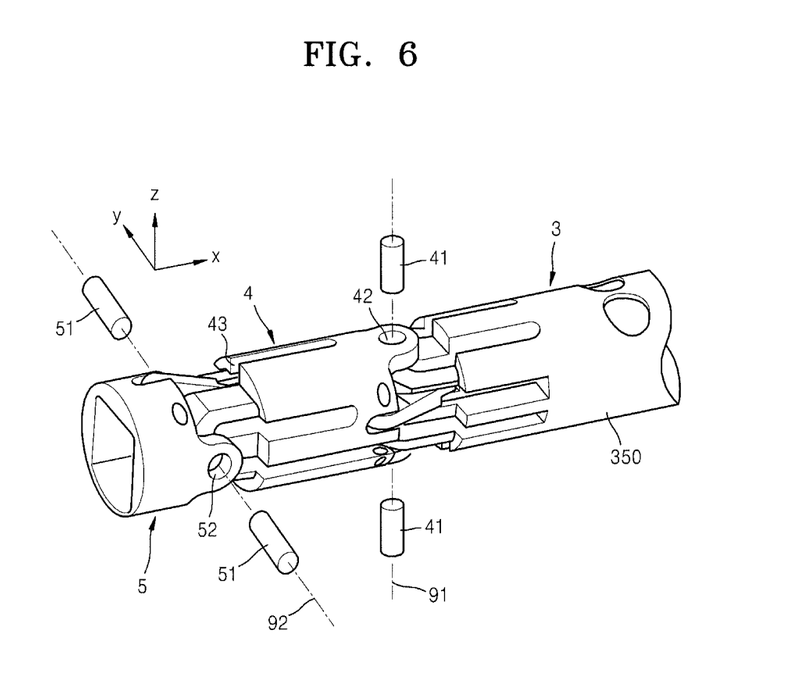
FIG. 6 is a perspective view of structures of first and second joint parts, according to another example embodiment.

The first joint part 4 is installed to rotate around the rotation axis 91 in the Z-direction with respect to the joint driving part 3. For example, referring to FIGS. 2 and 6, a base frame 350 may be arranged in the housing 310 of the joint driving part 3. The first joint part 4 and the base frame 350 are connected to each other via a pin 41. The pin 41 becomes the rotation axis 91 of the first joint part 4 in the Z-direction with respect to the joint driving part 3. For example, a diameter of the pin 41 may be less than a diameter of a through-hole 42 formed in the first joint part 4, so that the first joint part 4 may rotate around the pin 41. The pin 41 may be pressed and fixed in an insertion hole (not shown) of the base frame 350. Further, for example, a male screw (not shown) may be formed in an end of the pin 41, and a female screw (not shown) may be formed in the base frame 350, so that the pin 41 may be fixed in the base frame 350 via a screw connection. Moreover, the pin 41 may be adhered to an insertion hole (not shown) of the base frame 350. Here, the aforementioned rotatable connection structure of the first joint part 4 and the joint driving part 3 is an example and thus one or more embodiments are not limited thereto. In this regard, one of various rotatable connection structures that are well known in the art may be used.

The second joint part 5 is installed to rotate around the rotation axis 92 in the Y-direction with respect to the first joint part 4. For example, referring to FIG. 6, the first joint part 4 and the second joint part 5 are connected to each other via a pin 51. The pin 51 becomes the rotation axis 92 of the second joint part 5 with respect to the first joint part 4. For example, a diameter of the pin 51 may be less than a diameter of a through-hole 52 formed in the second joint part 5, so that the second joint part 5 may rotate around the pin 51. The pin 51 may be pressed and fixed in an insertion hole (not shown) of the first joint part 4. For example, a male screw (not shown) may be formed in an end of the pin 51, and a female screw (not shown) may be formed in the first joint part 4, so that the pin 51 may be fixed in the first joint part 4 via a screw connection. Further, the pin 51 may be adhered to an insertion hole (not shown) of the first joint part 4. Here, the aforementioned rotatable connection structure of the second joint part 5 and the first joint part 4 is an example and thus one or more embodiments are not limited thereto. Accordingly, one of various rotatable connection structures that are well known in the art may be used.

The first and second driving rods 110 and 120 are connected to the first and second joint parts 4 and 5 with respect to the link unit 400 (refer to FIG. 2). The link unit 400 includes first and second link units 410 (refer to FIG. 7) and 450 (refer to FIG. 10) for connecting the first and second driving rods 110 and 120 and the first and second joint parts 4 and 5, respectively.

Figure 7:
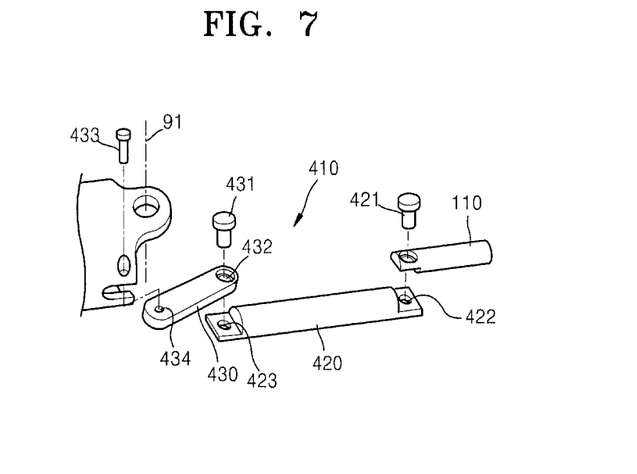
FIG. 7 is an exploded perspective view of a first link unit for driving the first joint part, according to another example embodiment.

The first link unit 410 may include a slider 420 connected to the first driving rod 110, and a link arm 430 connected to the slider 420 and the first joint part 4. The slider 420 may reciprocate in the X-direction. The slider 420 and the first driving rod 110 may be connected to each other by allowing a coupling member including a screw 421 to pass through the first driving rod 110 and the slider 420 and then to be coupled in a fixing hole 422 of the slider 420. The slider 420 and the first driving rod 110 may be fixed to each other.

The link arm 430 is rotatably connected to the slider 420. A rotation axis of the link arm 430 with respect to the slider 420 may be in the Z-direction that is the same as the direction of the rotation axis 91 of the first joint part 4. However, the direction of the rotation axis of the link arm 430 is not limited thereto, and thus, may be randomly set as long as the rotation axis of the link arm 430 may rotate the first joint part 4 with respect to the rotation axis 91. The link arm 430 and the slider 420 may be connected to each other via a pin 431 that is fixed to the slider 420 or the link arm 430 after the pin 431 passes through the slider 420 and the link arm 430. The pin 431 becomes the rotation axis of the link arm 430. For example, the pin 431 may be pressed into, may be screw-coupled to, or may be adhered to a fixing hole 423 of the slider 420 via a through-hole 432 of the link arm 430. A diameter of the pin 431 may be slightly less than a diameter of the through-hole 432 so that the link arm 430 may rotate with respect to the slider 420.

The aforementioned connection structure of the first driving rod 110, the slider 420, the link arm 430, and the first joint part 4 is an example, and thus, one or more embodiments are not limited thereto. In this regard, the first driving rod 110, the slider 420, the link arm 430, and the first joint part 4 may be sequentially connected according to one of various fixed or rotatable connection structures that are well known in the art.

A guide groove 351 for guiding the liner reciprocating movement of the slider 420 may be formed in the joint driving part 3. For example, referring to FIGS. 7 and 8, the guide groove 351 may be formed in the base frame 350 by being cut in the X-direction, that is, in the direction of the liner reciprocating movement of the slider 420. The pin 431 connecting the link arm 430 and the slider 420 may extend toward the base frame 350 and then may be inserted into the guide groove 351.

Figure 8:
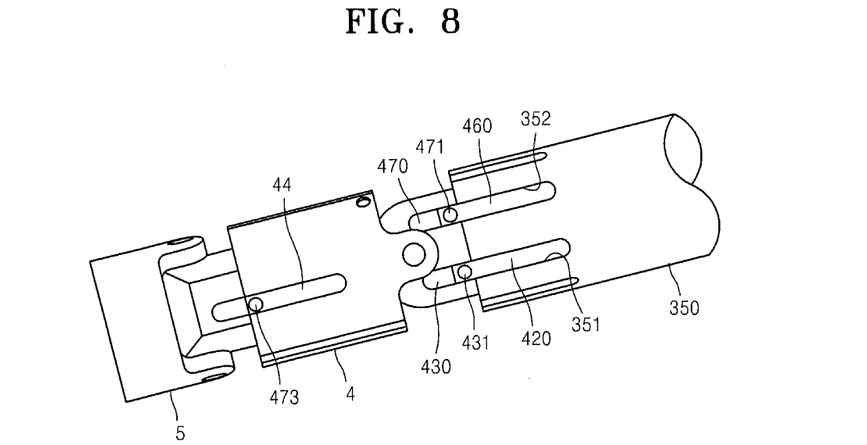
FIG. 8 is a rear view of the joint part.
Figure 9:
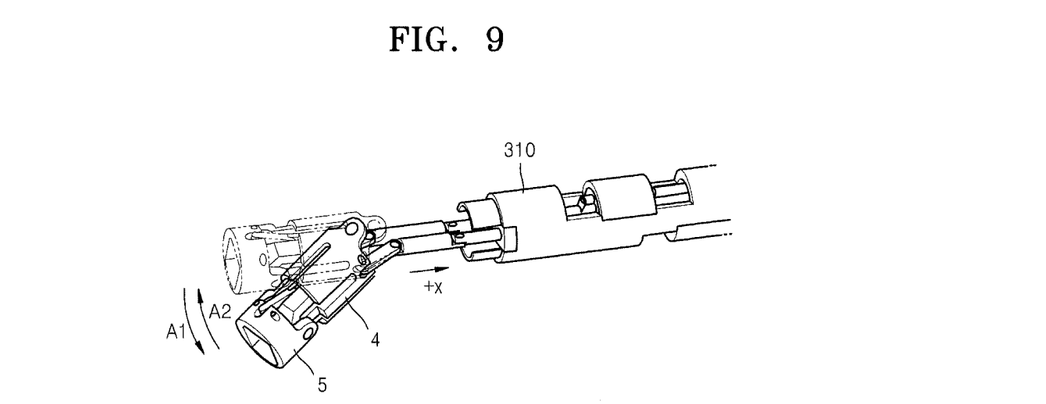
FIG. 9 is a perspective view illustrating a status in which the first joint part rotates.

Hereinafter, a process of rotating the first joint part 4 by using the aforementioned configuration will now be described. Referring to FIGS. 2, 8, and 9, the first joint part 4 is aligned in the −X direction. When the driving axis 131 is moved in the +X direction by driving the first linear motor 130, the first driving rod 110 pulls the slider 420 in the +X direction while the first driving rod 110 moves in the +X direction. The slider 420 is guided by the guide groove 351 and then reciprocates in the +X direction, so that the slider 420 pulls the link arm 430 in the +X direction. By doing so, the first joint part 4 rotates as illustrated in FIG. 9 in an arrow A1 direction. Since the link arm 430 and the slider 420 are rotatably connected to each other, the first joint part 4 may naturally rotate by using the pin 41 as the rotation axis 91. Conversely, in a status shown in FIG. 9, when the driving axis 131 is moved in the −X direction by driving the first linear motor 130, the first driving rod 110 and the slider 420 move in the −X direction, so that they push the link arm 430 in the −X direction. Then, the first joint part 4 rotates in an arrow A2 direction of FIG. 9 by using the pin 41 as the rotation axis 91. As described above, by reciprocating the first driving rod 110 by using the first linear motor 130, the first joint part 4 may rotate around the rotation axis 91 in the Z-direction.

Figure 10:
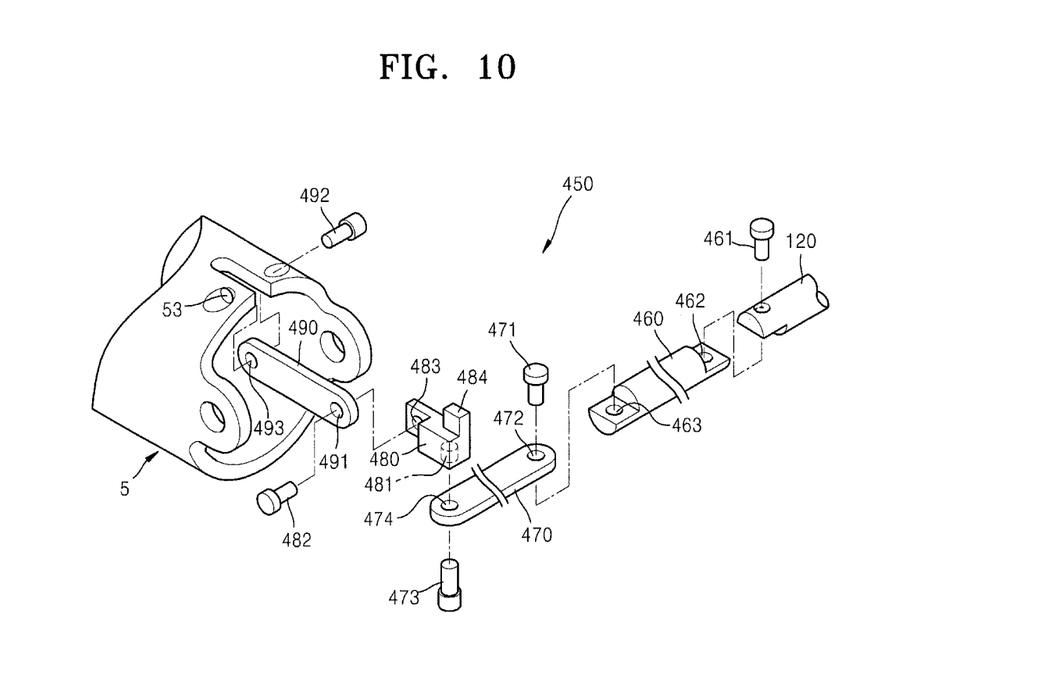
FIG. 10 is an exploded perspective view of a second link unit for driving the second joint part, according to another example embodiment.

Hereinafter, the second link unit 450 will now be described in detail with reference to FIG. 10. The second link unit 450 may include the second driving rod 120, a slider 460, and first through third link arms 470, 480, and 490. The slider 460 is connected to the first link arm 470, and the first link arm 470 extends to an inner portion of the first joint part 4 and then is connected to the second link arm 480. The second link arm 480 is connected to the third link arm 490 that is connected to the second joint part 5.

The slider 460 may reciprocate in the X-direction. For example, the slider 460 and the second driving rod 120 may be connected to each other by allowing a coupling member including a screw 461 to pass through the second driving rod 120 and the slider 460 and then to be coupled in a fixing hole 462. The slider 460 and the second driving rod 120 may be fixed to each other.

The first link arm 470 may be rotatably connected to the slider 460. The rotation axis of the first link arm 470 may be an axis in the Z-direction that is the same as the direction of the rotation axis 91 of the first joint part 4. The first link arm 470 and the slider 460 may be connected to each other via a pin 471 that is fixed to the slider 460 or the first link arm 470 after the pin 471 passes through the slider 460 and the first link arm 470. The pin 471 becomes the rotation axis of the first link arm 470. For example, the pin 471 may be pressed into, may be screw-coupled to, or may be adhered to a fixing hole 463 of the slider 460 via a through-hole 472 of the first link arm 470. A diameter of the pin 471 may be slightly less than a diameter of the through-hole 472.

The second link arm 480 may be rotatably connected to the first link arm 470. A direction of the rotation axis of the second link arm 480 with respect to the first link arm 470 may be in the Z-direction that is the same as the direction of the rotation axis 91 of the first joint part 4. The first link arm 470 and the second link arm 480 may be connected to each other via a pin 473 that is fixed to the first link arm 470 or the second link arm 480 after the pin 473 passes through the first link arm 470 and the second link arm 480. The pin 473 becomes the rotation axis of the second link arm 480. For example, the pin 473 may be pressed into, may be screw-coupled to, or may be adhered to a fixing hole 481 of the second link arm 480 via a through-hole 474 of the first link arm 470. A diameter of the pin 473 may be slightly less than a diameter of the through-hole 474.

The third link arm 490 may be rotatably connected to the second link arm 480. A direction of the rotation axis of the third link arm 490 with respect to the second link arm 480 may be in the Y-direction, that is, the same as the direction of the rotation axis 92 of the second joint part 5 but one or more embodiments are not limited thereto. The second link arm 480 and the third link arm 490 may be connected to each other via a pin 482 that is fixed to the second link arm 480 or the third link arm 490 after the pin 482 passes through the second link arm 480 and the third link arm 490. The pin 482 becomes the rotation axis of the third link arm 490 with respect to the second link arm 480. For example, the pin 482 may be pressed into, may be screw-coupled to, or may be adhered to a fixing hole 483 of the second link arm 480 via a through-hole 491 of the third link arm 490. A diameter of the pin 482 may be slightly less than a diameter of the through-hole 491.

The third link arm 490 and the second joint part 5 are connected to rotate with respect to each other. The third link arm 490 may be connected at an appropriate location so as to rotate the second joint part 5 with respect to the rotation axis 92. In the present embodiment, the third link arm 490 is connected to an upper portion of the second joint part 5 in the Z-direction. A pin 492 that passes through the third link arm 490 and the second joint part 5 may be coupled with the third link arm 490 or the second joint part 5. The pin 492 becomes a mutual rotation axis of the third link arm 490 and the second joint part 5. For example, the pin 492 may be pressed into, may be screw-coupled to, or may be adhered to a fixing hole 53 of the second joint part 5 via a through-hole 493 of the third link arm 490. A diameter of the pin 492 may be slightly less than a diameter of the through-hole 493.

The aforementioned connection structure of the second driving rod 120, the slider 460, the first through third link arms 470, 480, and 490, and the second joint part 5 is an example, and thus, one or more embodiments are not limited thereto. In this regard, the second driving rod 120, the slider 460, the first through third link arms 470, 480, and 490, and the second joint part 5 may be sequentially connected according to one of various fixed or rotatable connection structures that are well known in the art.

A guide groove 352 for guiding the liner reciprocating movement of the slider 460 may be formed in the joint driving part 3. For example, referring to FIGS. 8 and 10, the guide groove 352 may be formed in the base frame 350 by being cut in the X-direction. The pin 471 that connects the first link arm 470 and the slider 460 may extend toward the base frame 350 and then may be inserted into the guide groove 352.

The first link arm 470 extends to the inner portion of the first joint part 4 and then is connected to the second link arm 480. Portions of the second link arm 480 and the third link arm 490 may be disposed in the inner portion of the first joint part 4. In a case where the first joint part 4 rotates around the rotation axis 91, at least one of the first through third link arms 470, 480, and 490, and the first joint part 4 may interfere with each other, such that crosstalk may occur between the first joint part 4 and the second joint part 5. The crosstalk may be a disadvantageous factor in accurately controlling a rotation of each of the first joint part 4 and the second joint part 5. In order to decrease or to prevent the crosstalk, a sufficient space may be assured in the first joint part 4, so that the first through third link arms 470, 480, and 490, and the first joint part 4 may not interfere with each other while the first joint part 4 rotates. For this, it is necessary to increase a diameter of the first joint part 4, but this increase is not appropriate for the surgical device that is inserted into the human body. Thus, it is necessary to decrease or to prevent the crosstalk of the first and second joint parts 4 and 5 while the increase of the diameter of the first joint part 4 is restrained.

As described above, the first link arm 470 is rotatably connected to the slider 460. In order to allow the first link arm 470 to naturally rotate around the slider 460 with respect to the pin 471 when the first joint part 4 rotates around the rotation axis 91, the surgical device, according to the present embodiment, includes a connection unit. For example, the connection unit may include a second guide groove that is formed in the first joint part 4, and an insertion unit that is arranged in at least one of the first through third link arms 470, 480, and 490 and that is inserted into the second guide groove. For example, referring to FIGS. 2 and 6, the second guide groove may be a first cut groove 43 that is cut in a top portion of the first joint part 4 in the X-direction (a longitudinal direction of the first joint part 4). The insertion unit may be implemented by allowing a portion of the second link arm 480 or a portion of the third link arm 490 to be inserted into the first cut groove 43. For example, a projection part 484 (refer to FIG. 10) that extends upward may be arranged on the second link arm 480, as the insertion unit. Further, for example, referring to FIG. 8, the second guide groove may be a second cut groove 44 that is cut in a bottom portion of the first joint part 4 in the X-direction (the longitudinal direction of the first joint part 4). The insertion unit may be implemented by allowing the pin 473 connecting the second link arm 480 and the first link arm 470 to be extended and then to be inserted into the second cut groove 44. However, one or more embodiments are not limited to the aforementioned implementation of the connection unit, and thus, various examples having an equivalent implementation may be used.

Figure 11:
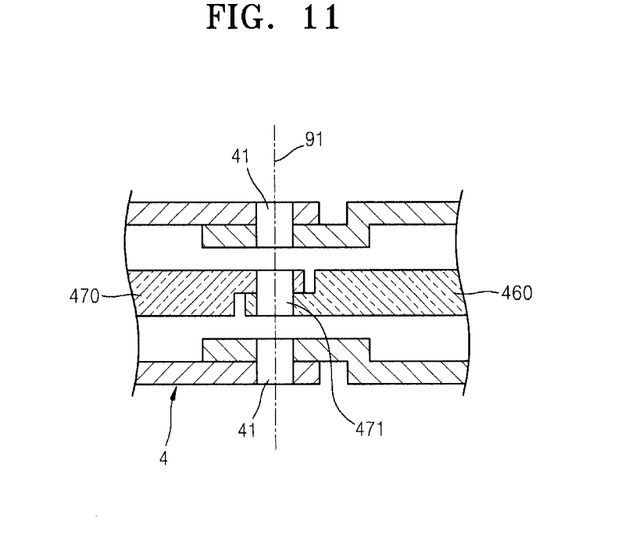
FIG. 11 is a cross-sectional view of an arrangement structure in which a rotation axis of the first joint part and a rotation axis of a first link arm are disposed so as to remove crosstalk between the first joint part and the second joint part.

By using the connection unit, the first link arm 470 rotates around the slider 460 when the first joint part 4 rotates, so that the crosstalk of the first joint part 4 and the second joint part 5 may be suppressed. As illustrated in FIG. 11, the crosstalk of the first joint part 4 and the second joint part 5 may be removed by matching the rotation axis of the first link arm 470 with respect to the slider 460 with the rotation axis 91 of the first joint part 4.

In a case where the rotation axis of the first link arm 470 with respect to the slider 460 does not match with the rotation axis 91 of the first joint part 4 due to spatial limitation, crosstalk that is proportional to a deviation amount between the two rotation axes may occur. According to the present embodiment, the second link arm 480 is rotatably connected to the first link arm 470 so as to rotate around the rotation axis in the Z-direction, and the second link arm 480 and/or the third link arm 490 are/is inserted into the first cut groove 43 that is formed in the top portion of the first joint part 4. In a case where the rotation axis of the first link arm 470 with respect to the slider 460, and the rotation axis 91 of the first joint part 4 deviate from each other, a rotation amount of the first joint part 4, and a rotation amount of the first link arm 470 with respect to the slider 460 do not match with each other, and the first cut groove 43 interferes with the second link arm 480 and/or the third link arm 490, or the insertion units arranged therein. Due to the interference, the second link arm 480 rotates around the rotation axis in the Z-direction with respect to the first link arm 470, and due to the rotation, crosstalk caused by the deviation amount between the two rotation axes may be significantly removed.

As described above, according to interaction between the first cut groove 43 and the insertion units, with respect to the first link arm 470, the second link arm 480 rotates around the rotation axis that is in parallel with the rotation axis 91 of the first joint part 4, so that the crosstalk due to the deviation between the rotation axis of the first link arm 470 with respect to the slider 460, and the rotation axis 91 of the first joint part 4 may be decreased.

Hereinafter, a process of rotating the second joint part 5 according to the aforementioned configuration will now be described. Referring to FIG. 2, the second joint part 5 is aligned in the −X direction.

Figure 12:
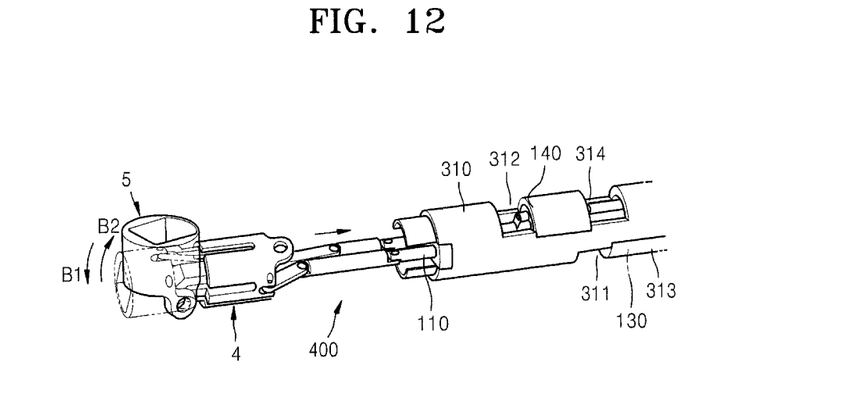
FIG. 12 is a perspective view illustrating a status in which the second joint part rotates.

When the driving axis 141 is moved in the +X direction by driving the second linear motor 140, the second driving rod 120 pulls the slider 460 in the +X direction while the second driving rod 120 moves in the +X direction. The slider 460 is guided by the guide groove 352 and then reciprocates in the +X direction, so that the first through third link arms 470, 480, and 490 are pulled in the +X direction. By doing so, as illustrated in FIG. 12 by an arrow B1, the second joint part 5 rotates around the rotation axis 92. Since the slider 460, and the first through third link arms 470, 480, and 490 are connected to sequentially rotate with respect to each other, the second joint part 5 may naturally rotate around the rotation axis 92. Conversely, in a status illustrated in FIG. 12, when the driving axis 141 is moved in the −X direction by driving the second linear motor 140, the second driving rod 120 and the slider 460 move in the −X direction and then push the first through third link arms 470, 480, and 490 in the −X direction. By doing so, the second joint part 5 rotates around the rotation axis 91 in an arrow B2 direction of FIG. 12. As described above, by reciprocating the second driving rod 120 by using the second linear motor 140, the second joint part 5 may rotate around the rotation axis 92 in the Y-direction. While the second joint part 5 rotates, reciprocating movement and rotating movement of the first through third link arms 470, 480, and 490 are limited by the second guide grooves (i.e., the first cut groove 43 and the second cut groove 44) that are formed in the first joint part 4, and as long as the second linear motor 140 is not driven, a rotation position of the first joint part 4 is not changed.

As described above, in the surgical device according to the present embodiment, the first joint part 4 and the second joint part 5 may be almost independently driven while crosstalk therebetween is prevented.

According to the present embodiment, the first joint part 4 and the second joint part 5 rotate around the rotation axes (refer to the first and second rotation axes 91 and 92) that are perpendicular to each other, but one or more embodiments are not limited thereto. Thus, the first joint part 4 and the second joint part 5 may rotate around rotation axes that are slanted with respect to each other by a random angle.

Figure 13:
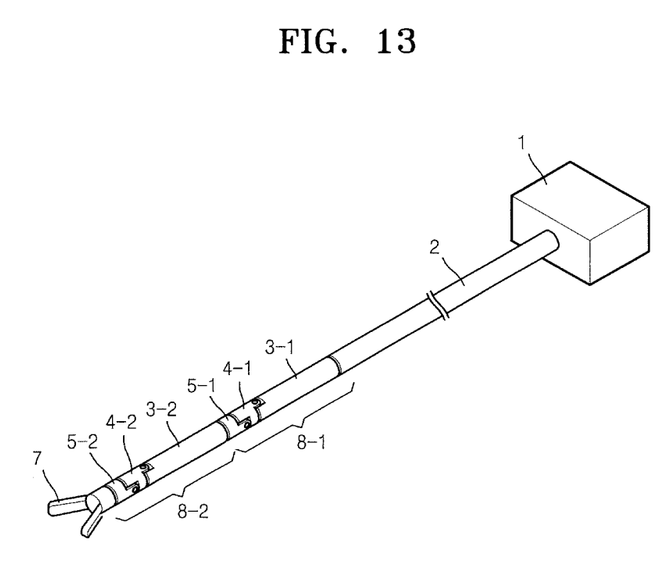
FIG. 13 is a perspective view illustrating a surgical device formed by serially connecting a plurality of joint assemblies, according to another example embodiment.

As described above, the present embodiment corresponds to a case in which the joint part 6 having two degrees of freedom is driven, but one or more embodiments are not limited thereto. As illustrated in FIG. 13, first and second joint assemblies 8-1 and 8-2 having a bar shape may be installed in series on the extension part 2. Each of the first and second joint assemblies 8-1 and 8-2 may have a structure as illustrated in FIGS. 1 through 12. Reference numerals 3-1 and 3-2 denote the joint driving part 3, reference numerals 4-1 and 4-2 denote the first joint part 4, and reference numerals 5-1 and 5-2 denote the second joint part 5. By combining the joint driving part 3-2 of the second joint assembly 8-2 with the second joint part 5-1 of the first joint assembly 8-1, the first and second joint assemblies 8-1 and 8-2 are connected in series. The surgical tool 7 is combined with the second joint part 5-2 of the second joint assembly 8-2.

By adjusting a combination direction of the first and second joint assemblies 8-1 and 8-2, that is, by adjusting a rotation combination angle with respect to an X-axis, it is possible to embody the surgical device having four degrees of freedom. FIG. 13 corresponds to a case in which the two joint assemblies are connected in series but if desired, it is possible to increase the number of degrees of freedom by serially connecting three or more joint assemblies. In the driving method using a cable according to the related art, the driver that drives the cable is mounted in the robot arm of the surgical robot, such that crosstalk between joints increases as the number of the joints is increased, an analysis therebetween is highly complicated, and thus, there is limitation in an increase of the number of the joints. However, according to one or more embodiments of the present disclosure, although a plurality of the joint assemblies are connected in series, the driving motor and a structure for driving a joint are installed in each of the joint assemblies, so that crosstalk between the driving of each of the joint assemblies significantly decreases. Accordingly, the surgical device according to one or more embodiments of the present disclosure may have highly excellent expandability in terms of the number of joints, and may assure independence of joint movement of each joint assembly.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A surgical device, comprising:
   a mounting part configured to mount on a robot arm of a surgical robot;
   an extension part extending from the mounting part;
   a plurality of joint assemblies sequentially connected from the extension part, one of the plurality of joint assemblies that is an outermost from among the plurality of joint assemblies being configured to have a surgical tool mounted thereto, each of the plurality of joint assemblies including:
   a joint driving part connected to an end of the extension part, the joint driving part including a driving motor and a driving rod which is a rigid body having a bar shape, the driving motor having a driving axis connected to the driving rod, the driving rod configured to reciprocate forward and backward in a longitudinal direction by the driving motor; and
   a joint part connected to the joint driving part via the driving rod such that, when the driving rod reciprocates in the longitudinal direction with respect to the joint part, the joint part is configured to drive at one or more degrees of freedom, wherein the joint driving part includes,
   a plurality of driving rods corresponding to the number of the one or more degrees of freedom of the joint part, and
   a plurality of driving motors configured to drive the plurality of driving rods.

2. The surgical device of claim 1, wherein the driving rod is connected to the driving axis with an elastic connection member, and the driving motor comprises:
   a linear motor that linearly reciprocates the driving axis, and wherein
   the elastic connection member includes first and second connecting members that each have first ends and second ends, and
   the first ends of the first and second connecting members are connected to the driving rod and the second ends of the first and second connecting members elastically contact ends of the driving axis in an axial direction of the driving axis.

3. The surgical device of claim 2, wherein the linear motor comprises an ultrasonic motor.

4. The surgical device of claim 1, wherein the driving rod is connected to the driving axis with an elastic connection member, and the driving motor comprises:
   a plurality of linear motors that linearly reciprocate the driving axis, and wherein
   the elastic connection member includes a plurality of first and second connecting members that each have first ends and second ends, and
   the first ends of the plurality of first and second connecting members are connected to the driving rod and the second ends of the plurality of first and second connecting members elastically contact ends of the driving axis in an axial direction of the driving axis.

5. The surgical device of claim 1, wherein the joint driving part comprises:
   a housing having a bar shape; and wherein
   the driving rod is mounted in the housing so as to reciprocate in the longitudinal direction of the housing by the driving motor, and the driving rod is connected to the joint part with one or more link arms.

6. The surgical device of claim 5, wherein the driving motor comprises:
   a linear motor fixed in the housing, the driving axis of the linear motor reciprocating in the longitudinal direction of the housing.

7. The surgical device of claim 6, wherein the driving rod is connected to the driving axis with an elastic connection member, and the elastic connection member includes first and second connecting members of which first ends are connected to the driving rod and of which second ends elastically contact ends of the driving axis while-applying a pre-load to ends of the driving axis.

8. The surgical device of claim 6, wherein
the driving rod is connected to the driving axis with an elastic connection member,
the driving motor includes a plurality of the linear motors, and
the elastic connection member includes a plurality of first and second connecting members that each have first and second ends, the first ends of the plurality of first and second connecting members being connected to the driving rod and the second ends of the plurality of first and second connecting members being elastically contacting ends of the driving axis while applying a pre-load to ends of the driving axis.

9. The surgical device of claim 8, wherein driving axes of the plurality of the linear motors are in parallel with a plurality of driving rods.

10. The surgical device of claim 1, wherein the driving motor comprises:
an ultrasonic motor.

11. The surgical device of claim 1, wherein the driving motor is connected to the driving axis with an elastic connection member.

12. The surgical device of claim 11, wherein the elastic connection member contacts an end of the driving axis while the elastic connection member applies a pre-load to the end of the driving axis.

13. A system, comprising:
a surgical robot including at least one robot arm; and
a surgical device mounted on the at least one robot arm, the surgical device including,
a mounting part configured to mount on the at least one robot arm;
an extension part to extend from the mounting part; and
a plurality of joint assemblies sequentially connected from the extension part, one of the plurality of joint assemblies that is an outermost from among the plurality of joint assemblies being configured to have a surgical tool mounted thereto, each of the plurality of joint assemblies including,
a joint driving part connected to an end of the extension part, the joint driving part including a driving motor and a driving rod which is a rigid body having a bar shape, the driving motor having a driving axis connected to the driving rod, the driving rod configured to reciprocate forward and backward in a longitudinal direction by the driving motor, and
a joint part connected to the joint driving part via the driving rod such that, when the driving rod reciprocates in the longitudinal direction with respect to the joint part, the joint part is configured to drive at one or more degrees of freedom, wherein the joint driving part includes,
a plurality of driving rods which correspond to the number of the one or more degrees of freedom of the joint part, and
a plurality of driving motors configured to drive the plurality of driving rods.

14. The system of claim 13, wherein the joint driving part comprises:
a housing having a bar shape; and wherein
the driving rod is mounted in the housing so as to reciprocate in a longitudinal direction of the housing by the driving motor, and the driving rod is connected to the joint part with one or more link arms.

15. The system of claim 14, wherein the driving motor comprises:
a linear motor fixed in the housing, the driving axis of the linear motor reciprocating in the longitudinal direction of the housing.

16. The system of claim 15, wherein a crosstalk between plural joint parts is removed by matching a rotation axis of at least one of the one or more link arms with a rotation axis of a respective joint part.

* * * * *